United States Patent [19]
Mishima et al.

[11] Patent Number: 5,262,153
[45] Date of Patent: Nov. 16, 1993

[54] SKIN-WHITENING AGENT

[75] Inventors: Yutaka Mishima, 4-32, 1-chome, Sowa-cho, Nada-ku, Kobe-shi, Hyogo; Yasuaki Oyama, Fukuoka; Masashi Kurimoto, Okayama, all of Japan

[73] Assignees: Kabushiki Kaisha Hayashibara Seibutsu Kagaku Kenkujo, Okayama; Sansho Seiyaku Kabushiki Kaisha, Fukuoka; Yutaka Mishima, Hyogo, all of Japan

[21] Appl. No.: 570,567

[22] Filed: Aug. 21, 1990

[30] Foreign Application Priority Data

Sep. 20, 1989 [JP] Japan .................. 1-241707

[51] Int. Cl.$^5$ ............................... A61K 7/021
[52] U.S. Cl. ........................ 424/62; 424/63; 424/403
[58] Field of Search ............ 424/62; 514/557, 784, 514/560, 785

[56] References Cited

U.S. PATENT DOCUMENTS

| | | | |
|---|---|---|---|
| 4,021,572 | 5/1977 | Van Scott et al. | 514/557 |
| 4,197,316 | 4/1980 | Yu et al. | 514/557 |
| 4,234,599 | 11/1980 | Van Scott et al. | 514/557 |
| 4,285,973 | 8/1981 | Edwards | 514/785 |
| 4,294,852 | 10/1981 | Wildnauer et al. | 514/557 |
| 4,363,815 | 12/1982 | Yu et al. | 514/557 |
| 4,393,043 | 7/1983 | Koulbanis et al. | 424/81 X |
| 4,608,370 | 8/1986 | Aronsohn | 514/557 |

FOREIGN PATENT DOCUMENTS 45510 2/1987 Japan .
284109 11/1988 Japan .

OTHER PUBLICATIONS

Drug Facts and Comparisons, 1990 Ed. Lippincott Co., p. 2085.

*Primary Examiner*—Thurman K. Page
*Assistant Examiner*—Neil Levy
*Attorney, Agent, or Firm*—Sheridan Neimark

[57] ABSTRACT

Lactic acid and its derivatives such as D-lactic acid, L-lactic acid, DL-lactic acid, and their nonmetallic derivatives and lactates of alkali metal or alkaline earth metal exhibit a strong skin-whitening effect at a concentration of 5 w/w % or higher in pigment cell. The skin-whitening effect is augmented by unsaturated fatty acids having a carbon number of 12–22.

11 Claims, No Drawings

SKIN-WHITENING AGENT

BACKGROUND OF THE INVENTION

1. Field of the Invention

The present invention relates to a skin-whitening agent, in particular, to a novel skin-whitening agent which is not intended to inhibit the function and activity of tyrosinase, but intended to suppress the formation of tyrosinase, i.e. suppressing melanogenesis by preventing the formation of tyrosinase per se.

2. Description of the Prior Art

Melanin, which usually occurs in the skin, plays an important role in the protection of the human body from ultra-violet rays, as well as being very important as a medical and cosmetical factor. Melanin is synthesized by tyrosinase in dermal pigment cell through the convertion of tyrosine into dopa, dopa quinone and 5,6-dyhydroxiindole in the given order. Excessive pigmentation may result in dark skin, and its local occurrence may lead to chloasma or freckle, which are all cosmetically defective.

Conventionally, hydroquinone and MBEH (monobenzylether of hydroquinone) have been used to realize beautiful clear skin: These compounds bear a strong skin-whitening ability which is however mainly due to denaturation and death of pigment cell. Thus, the use of these compounds may damage dermal physiology to elicit undesirable side effects such as irreversible leukoderma, pigmentary disorder and contact dermatitis.

In view of the foregoing, Japanese Patent Kokai 53-142515 first highlighted tyrosinase as a factor which is responsible for melanogenesis, as well as proposing the use of vitamin C, glutathione and cysteine in order to reduce dermal melanin for the realization of beautiful clear skin.

Each of these compounds however acts as a tyrosinase inhibitor which inhibits the activity and function of a tyrosinase which has been formed. As mentioned above, prior art has been focused on the way of inhibiting the activity of tyrosinase.

While the skin-whitening agent of this invention is intended to prevent the formation of tyrosinase, but unlike prior art not concerns the way of treating formed tyrosinase. In other words, we draw attention to tyrosinase which is the root cause of cosmetical troubles, and the skin-whitening agent of this invention is directed to the most fundamental part of the melanogenic system, i.e. suppressing the formation of tyrosinase.

Since such a skin-whitening agent has never proposed, this technical object is deemed to be novel. To attain such a novel object, this invention employs as the effective component at least one member selected from lactic acid, lactates of alkali metal or alkaline earth metal, and nonmetallic derivatives of lactic acid at a concentration of 5 w/w % or higher optionally with an unsaturated fatty acid. Prior art teaches and discloses nothing about this technical concept. The skin-whitening agent of this invention is therefore entirely novel.

For this reason, this invention is novel in object and elements, and the advantage is therefore novel and remarkable.

SUMMARY OF THE INVENTION

As described heretofore, conventional tyrosinase inhibitors are unstable because they are all reductants and utilize their reducing power, as well as being insufficient in tyrosinase inhibitory activity, its prolongation and skin-whitening activity in viable cells (Japanese Patent Kokai 53-142515, page 1, right lower corner through page 2, left upper corner).

This invention is to completely overcome the above described drawbacks of prior art. As long as conventional approach to tyrosinase inhibitory substance is made, it would be impossible to find out any substance which attains desired tyrosinase inhibitory activity and its prolongation.

We extensively investigated various substances from many different aspects, and came to the conclusion that no medicine completely would attain the object if tyrosinase has been once formed.

We understood at last that, if the formation of tyrosinase is prevented, then no cosmetical trouble occur because tyrosinase per se is responsible for the trouble. Thus, we changed our approach, and set an entirely novel technical object, i.e. development of a skin-whitening agent which is tyrosinase formation suppressive.

To realize the object, we screened various substances with potential tyrosinase formation-suppressive activity (referred to as "tyrosinase formation-suppressive substance" hereinafter), in particular, highly-stable metabolic organic acids and fatty acids which do not directly inhibit tyrosinase, but do suppress the formation of tyrosinase while utilizing the independent melanogenic controlling function of viable pigment cell.

As the result, we discovered that one or more members selected from lactic acid, lactates of alkali metal or alkaline earth metal, and nonmetallic derivatives of lactic acid strongly suppress the formation of tyrosinase alone or together with an unsaturated fatty acid, as well as confirming that these compounds are suitable as the tyrosinase formation-suppressive substance.

Also was found that a skin-whitening agent containing either of these lactic acid and its derivatives at a concentration of at least 5 w/w % exhibits a significant melanogenesis suppressive activity which results in a skin-whitening effect.

DETAILED DESCRIPTION OF THE INVENTION

The wording "lactic acid and its derivatives" as referred to in this invention includes lactic acids such as L-lactic acid, D-lactic acid and DL-lactic acid; their lactates of alkali metal or alkaline earth metal such as sodium lactate, potassium lactate, calcium lactate and magnesium lactate; and nonmetallic derivatives of the lactic acids such as ammonium lactate, lactic acid ester and lactic acid amide.

The wording "unsaturated fatty acid" as referred to in this invention means those with a carbon number of 12-22, for example, carboxylic acids such as lauroleic acid ($C_{12:1}$), myristoleic acid ($C_{14:1}$), pentadecenoic acid ($C_{15:1}$), hexadecenoic acid ($C_{16:1}$), palmitoleic acid ($C_{16:1}$), oleic acid ($C_{18:1}$), ricinoleic acid ($C_{18:1}$), linoleic acid ($C_{18:2}$), linolenic acid ($C_{18:3}$), gadoleic acid ($C_{20:1}$), arachidonic acid ($C_{20:4}$), eicosatetraenoic acid ($C_{20:4}$), eicosapentaenoic acid ($C_{20:5}$), erucic acid ($C_{22:1}$), clupanodonic acid ($C_{22:5}$), and their salts.

The skin-whitening agent of this invention is characterized in that it substantially does not inhibit tyrosinase although it exhibits a superior tyrosinase formation-suppressive activity in viable cells.

The assay methods used in this invention are as follows:

(1) Tyrosinase inhibitory activity is assayed in accordance with the method described in *British Journal of Dermatology*, Vol. 103, pp. 625-633 (1980) with a slight modification. In this method, a test specimen is allowed to react while keeping a prescribed pH. When the tyrosinase activity in the test specimen is reduced as compared with control, the test specimen is deemed to be "tyrosinase inhibitory".

(2) Melanogenesis suppressive activity in pigment cell is assayed in accordance with the method described in *Cancer Research*, Vol. 42, pp. 1994-2002 (1982) with a slight modification. $4 \times 10^4$ B-16 cells, a mouse melanoma strain, are suspended in 10 ml Eagle's MEM containing 10 v/v % fetal calf serum, transferred to 25 cm² Roux's flask, and cultured at 37° C. in the presence of 5 v/v % $CO_2$. The culture is continued for 5 days while refreshing the culture medium with fresh one additionally containing a test specimen on the starting and third days. After washing in phosphate buffer (pH 7.2) containing 0.8 w/v % saline, the cells are detached with a solution containing trypsin and EDTA, and recovered by filtration. The cells on the filter paper are then dried, and determined for the strength of reflected light at 500 nm using a densitometry.

The total amount of melanin is estimated with absorbance by reflected light (degree of darkness).

When the absorbance in the treated group is reduced under these conditions to 80% or lower of control, the treated group is deemed to be "melanogenesis suppressive", i.e. exhibiting skin-whitening activity.

(3) Tyrosinase formation-suppressive activity is assayed in accordance with the dopa reaction method described in *Nippon Hifuka Gakkai Zasshi (Japanese Journal of Dermatology)*, Vol. 87, No. 13, pp. 883-901 (1977) and also with the tyrosinase confirming method described in *Cancer Research*, Vol. 42, pp. 1994-2002 (1982) with a slight modification. Mouse melanoma M-16 cell is whitened by culturing it in a culture medium containing a melanogenesis suppressive substance of this invention similarly as above for 5 days, and the culture medium is then removed. The residue is fixed in 10 v/v % formalin, and soaked in 0.1M phosphate buffer (pH 7.3) containing 0.1 w/v % L-dopa at 37° C. for 3 hours. When microscopic and electrophoretic observations confirm that the cell has undergone no pigmentation and that all the tyrosinase isozymes $T_1$, $T_2$ and $T_3$ have reduced or diminished, the substance is deemed to be "tyrosinase formation suppressive".

The lactic acid and its derivatives used in this invention are all tyrosinase formation-suppressive substances bearing both wide safety margin and high stability. The skin-whitening agent containing such a lactic acid or derivative at a concentration of 5-50 w/w %, desirably, 8-30 w/w % optionally with an unsaturated fatty acid is favorably usable in medicines, for example, those in ointment, emulsion or lotion form, as well as in cosmetics, for example, milky lotion, pack and cream.

The skin-whitening agent of this invention is very efficacious in the treatment and prevention of pigmentation such as chloasma, freckle and sunburn because it does suppress the melanogenesis and exhibit a significant skin-whitening activity.

The above described lactic acid and derivatives are usable alone or in mixture, and the latter way of use may result in a synergism.

The lactic acid, derivatives and unsaturated fatty acids should be substantially nontoxic as those from bioelements or other natural sources.

The following experiments will explain this invention in detail.

EXPERIMENT 1

Screening of tyrosinase formation-suppressive substance in vitro

Experiment 1(1)

Organic acids

The metabolic organic acids as listed in Table I were tested for their tyrosinase inhibitory activity, melanogenesis suppressive activity and tyrosinase formation-suppressive activity by the methods described heretofore. Each organic acid was first neutralized with sodium hydroxide to a prescribed pH, then adjusted to a concentration of 0.5 w/w %, prior to its use.

TABLE I

| Organic acids | Tyrosinase inhibitory activity | Melanogenesis suppressive activity | Tyrosinase formation-suppressive activity |
|---|---|---|---|
| Lactid acid | − | + | + |
| Asparaginic acid | − | − | − |
| Glutamic acid | − | − | − |
| Citric acid | − | − | − |
| Fumaric acid | − | − | − |
| Malic acid | − | − | − |
| Vitamin C | + | − | − |

Note: When optical isomers were available, L-isomer was used. (+) means that inhibitory or suppressive activity was noted, while (−) means that neither inhibitory nor suppressive activity was noted.

The results in Table I evidently confirm that unlike other organic acids, lactic acid exhibits a significant tyrosinase formation-suppressive activity although it exhibits no tyrosinase inhibitory activity.

Also is confirmed that lactic acid exhibits a significant melanogenesis-suppressive activity, i.e. skin-whitening activity.

Experiment 1(2)

Lactic acid and its derivatives

Lactic acid and its derivatives were tested for their tyrosinase inhibitory activity, melanogenesis suppressive activity and tyrosinase formation-suppressive activity by the methods in Experiment 1(1) with a slight modification.

The results were as shown in Table II.

TABLE II

| Lactic acid and derivatives | Tyrosinase inhibitory activity | Melanogenesis suppressive activity | Tyrosinase formation-suppressive activity |
|---|---|---|---|
| L-Lactic acid | − | + | + |
| Sodium DL-lactic acid | − | + | + |
| Potassium L-lactate | − | + | + |
| Megnesium DL-lactate | − | + | + |
| Calcium L-lactate | − | + | + |
| Ammonium DL-lactate | − | + | + |
| Ethyl L-lactate | − | + | + |
| L-Lactic acid amide | − | + | + |

Note: (+) means that inhibitory or suppressive activity was noted, while (−) means that neither inhibitory nor suppressive activity was noted.

The results in Table II evidently confirm that as is the case of L-lactic acid, lactates of alkali metal such as sodium DL-lactate and potassium L-lactate, lactates of alkaline earth metal such as magnesium DL-lactate and calcium L-lactate, and nonmetallic derivatives of lactic acid such as ammonium DL-lactate, ethyl L-lactate and L-lactic acid amide all exhibit a significant tyrosinase formation-suppressive activity although they exhibit no tyrosinase inhibitory activity.

Also is confirmed that these lactic acid and derivatives all exhibit a significant melanogenesis suppressive activity, i.e. skin-whitening activity.

Experiment 1(3)

Fatty acids

The fatty acids as listed in Table III were tested for their tyrosinase inhibitory activity, melanogenesis suppressive activity and tyrosinase formation-suppressive activity by the methods in Experiment 1(1) with a slight modification. Each fatty acid was first neutralized with sodium hydroxide to a prescribed pH, then adjusted to a concentration of 0.01 w/w %, prior to its use.

The results were as shown in Table III.

TABLE III

| Fatty acids | Tyrosinase inhibitory activity | Melanogenesis suppressive activity | Tyrosinase formation-suppressive activity |
|---|---|---|---|
| Saturated fatty acids | | | |
| Lauric acid ($C_{12}$) | − | − | − |
| Myristic acid ($C_{14}$) | − | − | − |
| Palmitic acid ($C_{16}$) | − | − | − |
| Stearic acid ($C_{18}$) | − | − | − |
| Arachic acid ($C_{20}$) | − | − | − |
| Behenic acid ($C_{22}$) | − | − | − |
| Lignoceric acid ($C_{24}$) | − | − | − |
| Unsaturated fatty acids | | | |
| Lauroleic acid ($C_{12:1}$) | − | + | + |
| Myristoleic acid ($C_{14:1}$) | − | + | + |
| Pentadecenoic acid ($C_{15:1}$) | − | + | + |
| Palmitoleic acid ($C_{16:1}$) | − | + | + |
| Oleic acid ($C_{18:1}$) | − | + | + |
| Ricinoleic acid ($C_{18:1}$) | − | + | + |
| Linoleic acid ($C_{18:2}$) | − | + | + |
| Linolenic acid ($C_{18:3}$) | − | + | + |
| Gadoleic acid ($C_{20:1}$) | − | + | + |
| Arachidonic acid ($C_{20:4}$) | − | + | + |
| Eicosatetraenoic acid ($C_{20:4}$) | − | + | + |
| Eicosapentaenoic acid ($C_{20:5}$) | − | + | + |
| Erucic acid ($C_{22:1}$) | − | + | + |
| Clupanodonic acid ($C_{22:5}$) | − | + | + |

Note: (+) means that inhibitory or suppressive activity was noted, while (−) means that neither inhibitory nor suppressive activity was noted.

The results in Table III evidently confirm that unlike saturated fatty acids, unsaturated fatty acids exhibit a significant tyrosinase formation-suppressive activity although they exhibit no tyrosinase inhibitory activity.

Also is confirmed that these fatty acids exhibit a significant melanogenesis suppressive activity, i.e. skin-whitening activity.

EXPERIMENT 2

Skin-whitening effect in vivo

The lactic acid, derivatives and unsaturated fatty acids which had marked a significant tyrosinase formation-suppressive activity in vitro in Experiment 1 were further tested for their skin-whitening activity in vivo. The lactic acid and derivatives were particularly determined for their effective type and concentration.

Healthy male and female volunteers (20–50 year old) received about 0.6 J ultraviolet irradiation at two different spots in their brachial area, 2.25 $cm^2$ each, once every day for 3 days, and a skin-whitening agent was applied on either irradiated spot 3 times every day over 24 days. Thereafter, the irradiated spot with the skin-whitening agent was compared with control to estimate the degree of melanogenic suppression, i.e. skin-whitening effect.

The skin-whitening agent was prepared by mixing 10 parts by weight of ethanol and 0.18 parts by weight of methyl p-hydroxybenzoate together with either 0 (control), 4, 10, 16 or 40 parts by weight of 50 w/w % of either lactic acid or derivative as listed in Table IV, adjusting the mixture to pH 5.5 with 10 w/w aqueous citric acid solution, and pouring refined water to the mixture to give a total amount of 100 parts by weight.

The concentration of lactic acid or derivative in the skin-whitening agent was therefore 0 w/w % (control), 2 w/w %, 5 w/w %, 8 w/w % or 20 w/w %.

The skin-whitening agent was applied by first soaking it in gauze, then attaching the gauze over an irradiated spot in accordance with the occlusive dressing technique.

Skin-whitening effect was determined by comparing the treated spot with control for their melanogenic suppression, i.e. skin-whitening effect; grading the skin-whitening effect into either "superior", "not changed" or "inferior"; and numerating the volunteers answering "superior" (20 volunteers in each group).

The results were as shown in Table IV.

TABLE IV

| Lactates and derivatives | Concentration (w/w %) | | | |
|---|---|---|---|---|
| | 2.0 | 5.0 | 8.0 | 20.0 |
| Sodium L-lactate | 7 | 16 | 19 | 20 |
| Magnesium L-lactate | 6 | 15 | 18 | 20 |
| Ammonium DL-lactate | 7 | 15 | — | 20 |
| Sodium L-lactate + 0.01 w/w % pentadecenoic acid | 12 | 20 | — | 20. |
| Remark | Control | Present invention | Present invention | Present invention |

Note: (—) means "not done".

The results in Table IV evidently confirm that the skin-whitening agent containing lactic acid or its derivative exhibits a significant skin-whitening activity at a concentration of 5 w/w % or higher.

Also is confirmed that the skin-whitening activity is augmented by the combination with unsaturated fatty acids.

As obvious from the above Experiments, the skin-whitening agent of this invention exhibits both tyrosinase formation-suppressive and melanogenesis suppressive activities which result in a high skin-whitening effect. Furthermore, the skin-whitening agent would have a wide safety margin because of its effective dose and administration route.

Although one or more members selected from lactic acid, lactates of alkali metal or alkaline earth metal, and nonmetallic derivatives of lactic acid optionally with an unsaturated fatty acid can be used alone as the skin-whitening agent of this invention, the concentration of such a lactic acid or derivative is usually set in the range of 5.0–50 w/w %, desirably, 8.0–30 w/w %, while the pH level is usually set in the range of 2.5–9.0, desirably, 3.0–8.0. The dose for adult per day should be adequately changed in the range of 0.1 g to 500 g based on tyrosinase formation-suppressive substance dependently on the administration route and patient's symptom.

To maximize the efficacy in the treatment and prevention of local and systemic pigmentation such as chloasma, freckle, sunburn and addisonism, the skin-whitening agent containing tyrosinase formation-suppressive substance(s) alone or in combination with any desirable material, for example, bioactive substance, nutrient, penetration accelerant, stabilizer, carrier and vehicle, can be freely prepared into an adequate form to meet to its final uses such as medicinal and cosmetic uses.

Conventional alcohols and surfactants are feasible as the penetration accelerant.

The skin-whitening agent of this invention is usable in medicines for external use such as those in lotion, milky lotion, cream, ointment and cataplasm form, as well as in cosmetics such as beauty wash, milky lotion, pack and cream.

In use, iontophoresis may facilitate the penetration of a tyrosinase formation-suppressive substance into a deeper part of the skin, and the effect may be improved by the use of an appropriate supporting electrolyte. Such an iontophoresis is favorably used to augment both tyrosinase formation-suppressive and melanogenesis suppressive activities, i.e. to attain a higher skin-whitening effect.

If necessary, one or more members, for example, of vitamin C, vitamin E, glutathione, cysteine, placental extract, "Kankho-so No. 201 (a photosensitive dye commercialized by Nippon Kankoh-Shikiso Kenkyujo Co., Ltd., Okayama, Japan)", colloidal sulfer and hydroquinone derivative can be freely incorporated together with tyrosinase formation-suppressive substance(s) for a much effective melanogenic suppression and consequently an increased skin-whitening effect. One or more appropriate sunscreen agents can be freely used in combination so that the skin-whitening effect of the skin-whitening of this invention is further augmented.

Several embodiments of this invention will be described hereinafter.

EXAMPLE 1

Medicine for external use (Ointment)

One part by weight of sodium L-lactic acid, 4.0 parts by weight of calcium DL-lactate and 5.0 parts by weight of glycerine were mixed to homogeneity, and the mixture was added to another mixture of 10.0 parts by weight of vaseline, 5.0 parts by weight of Japan wax, 5.0 parts by weight of lanolin, 1.0 part by weight of pentadecenoic acid and 0.1 part by of mint oil, followed by kneading to homogeneity.

The product is favorably usable as a skin-whitening agent directed to treatment and prevention of local and systemic pigmentation such as chloasma, freckle, sunburn and addisonism.

EXAMPLE 2

Medicine for external use (Emulsion)

Four parts by weight of ammonium DL-lactate and 6.0 parts by eight of L-lactic acid were mixed with 12.0 parts by weight of liquid paraffin, 4.0 parts by weight of lanolin, 3.5 parts by weight of oleic acid, 1.0 part by weight of triethanolamine and 3.0 parts by weight of octyldodecyl myristate to homogeneity in usual manner, and the mixture was added with 66.5 parts by weight of refined water and appropriate amounts of antiseptic and flavoring agent, and emulsified with a homogenizer.

The product is favorably usable as a skin-whitening agent directed to the treatment and prevention of pigmentation similarly as the product in Example 1.

EXAMPLE 3

Medicine for external use (Lotion)

Twenty parts by weight of sodium L-lactate, 8.0 parts by weight of polyoxyethylene-hardened castor oil, 15.0 parts by weight of ethanol, 4.0 parts by weight of 1,3-butylene glycol, 0.1 part by weight of p-hydroxybenzoic acid, 0.1 part by weight of citric acid, 0.3 parts by weight of sodium citrate, 0.01 part by weight of EDTA-$Na_2$ and 52.4 parts by weight of refined water were mixed to homogeneity in usual manner.

The product is favorably usable as a skin-whitening agent directed to the treatment and prevention of pigmentation such as chloasma, freckle and sunburn similarly as the product in Example 1.

EXAMPLE 4

Medicine for external use (Cataplasm)

Ten parts by weight of 50 w/w % sodium lactate, 20 parts by weight of glycerin, 7 parts by weight of sodium polyacrylate, 4 parts by weight of titanic oxide and 0.3 parts by weight of aluminum chloride were mixed while heating, and the mixture was added to a heated mixture of 30 parts by weight of polyacrylic acid, 1 part by weight of sorbitan monooleate and 27.7 parts by weight of refined water to homogeneity. The resultant was cooled and applied on one side of a lint which was then attached with a liner and cut into square.

The product is favorably usable as a skin-whitening agent in the treatment and prevention of pigmentation such as chloasma, freckle and sunburn similarly as the product in Example 1.

EXAMPLE 5

Cosmetic (Milky lotion)

One half part by weight of polyoxyethylene behenyl ether, 1.0 part by weight of polyoxyethylene sorbitol tetraoleate, 1.0 part by weight of lipophilic glycerine monostearate, 0.5 parts by weight of behenyl alcohol, 1.0 part by weight of avocado oil, 1.0 part by weight of linoleic acid and appropriate amounts of vitamin E and antiseptic were dissolved in usual manner by heating, and the resultant mixture was added with 6.5 parts by weight of sodium L-lactate, 5.0 parts by weight of 1,3-butylene glycol, 0.1 part by weight of caboxyvinyl polymer and 80.3 parts by weight of refined water. The resultant was emulsified with a homogenizer, and added with an appropriate amount of flavoring agent while stirring.

The product is favorably usable as a skin-whitening agent directed to the treatment and prevention of pigmentation such as chloasma, freckle and sunburn.

EXAMPLE 6

Cosmetic (Pack)

One half part by weight of linolenic acid was mixed with 1.5 parts by weight of squalane, 0.5 parts by weight of polyoxytheylene-hardened castor oil, 5.5 parts by weight of sodium L-lactate, 4.0 parts by weight of glycerine, 15.0 parts by weight of polyvinyl alcohol, 10.0 parts by weight of ethanol and 63.0 parts by weight of refined water in usual manner to homogeneity.

The product is favorably usable as a skin-whitening agent directed to the treatment and prevention of pigmentation similarly as the product in Example 4.

EXAMPLE 7

Cosmetic (Cream)

Two parts by weight of polyoxyethylene glycol monostearate, 5 parts by weight of self-emulsifying glycerine monostearate, 5 parts by weight of potassium DL-lactate, 1 part by weight of behenyl alcohol, 2.0 parts by weight of eicosatetraenoic acid, 1 part by weight of liquid paraffin, 10 parts by weight of glycerine trioctanate and an appropriate amount of antiseptic were dissolved in usual manner by heating, and the mixture was added with 2 parts by weight of L-lactic acid, 5 parts by weight of 1,3-butylene glycol and 66 parts by weight of refined water, emulsified with a homogenizer, and further added with an appropriate amount of flavoring agent while stirring.

The product is favorably usable as a skin-whitening agent directed to the treatment and prevention of pigmentation similarly as the product in Example 4.

As described heretofore, we discovered that 5 w/w % or more, desirably, 8 w/w % or more of one or more members of lactic acid, lactates of alkali metal or alkaline earth metal, and nonmetallic derivatives of lactic acid optionally with an unsaturated fatty acid exhibits a strong tyrosinase formation-suppressive activity in pigment cell although these compounds do not inhibit tyrosinase. Based on this finding, we established a skin-whitening agent which contains any of these tyrosinase formation-suppressive substances as the effective component.

Furthermore, since the skin-whitening agent of this invention exhibits a strong melanogenesis suppressive activity and consequently attains a skin-whitening effect, it is favorably usable in medicines such as those in ointment, emulsion or lotion form, as well as in cosmetics such as milky lotion, pack and cream in the treatment and prevention of local and systemic pigmentation such as chloasma, freckle, sunburn and addisonism.

In addition, the skin-whitening agent of this invention is highly safe and usable without special care in view of its effective dose and administration route because the lactic acid, derivatives and unsaturated fatty acids are all metabolic substances with a wide safety margin. Also, high resistance to both heat and pH of the skin-whitening agent facilitates its sterilization and long-term storage. These are indispensable futures in manufacturing and extensive application. Thus, this invention would be significant in the art.

We claim:

1. A method to whiten the skin, said method containing the step of administering an effective amount of a skin-whitening agent which contains as the effective component at least 5 w/w % of a member selected from the group consisting of lactic acid, lactate of alkali metal or alkaline earth metal, ammonium lactate, lactic acid ester, lactic acid amide, and mixtures thereof in order to suppress the formation of tyrosinase.

2. The method of claim 1, wherein said lactic acid is a member selected from the group consisting of L-lactic acid, D-lactic acid, and mixture thereof.

3. The method of claim 1, wherein said lactate of alkali metal or alkaline earth metal is a member selected from the group consisting of sodium lactate, potassium lactate, calcium lactate, magnesium, and mixtures thereof.

4. The method of claim 1, wherein said agent additionally contains an unsaturated fatty acid having a carbon number in the range of 12-22.

5. The method of claim 1, wherein said agent additionally contain an unsaturated fatty acid selected from the group consisting of lauroleic acid ($C_{12:1}$), myristoleic acid ($C_{14:1}$), pentadecenoic acid ($C_{15:1}$), hexadecenoic acid ($C_{16:1}$), palmitoleic acid ($C_{16:1}$), oleic acid ($C_{18:1}$), ricinoleic acid ($C_{18:1}$), linoleic acid ($C_{18:2}$), linolenic acid ($C_{18:3}$), gadoleic acid ($C_{20:1}$), arachidonic acid ($C_{20:4}$), eicosatetraenoic acid ($C_{20:4}$), eicosapentaenoic acid ($C_{20:5}$), erucic acid ($C_{22:1}$), clupanodonic acid ($C_{22:5}$), their salts, and mixtures thereof.

6. The method of claim 1, wherein the dose for adult is in the range of 0.1–500 g per day.

7. The method of claim 1, wherein the pH of said agent is set in the range of 2.5–9.0.

8. The method of claim 1, wherein said agent is a medicine for external use.

9. The method of claim 8, wherein said agent is in ointment, lotion, emulsion or cataplasm form.

10. The method of claim 1, wherein said agent is a cosmetic.

11. The method of claim 10, wherein said agent is in milky lotion, pack or cream form.

* * * * *